United States Patent
Pallaro et al.

(10) Patent No.: US 7,460,161 B2
(45) Date of Patent: Dec. 2, 2008

(54) MULTIFUNCTIONAL INTEGRATED VISUAL SYSTEM WITH CMOS OR CCD TECHNOLOGY MATRIX

(75) Inventors: Nereo Pallaro, Orbassano (IT); Filippo Visintainer, Orbassano (IT); Piermario Repetto, Turin (IT); Elena Borello, Rubiana (IT); Bartolomeo Pairetti, Barge (IT); Stefano Bernard, Turin (IT)

(73) Assignee: CRF Societa Consortile Per Azioni, Turin (IT)

( * ) Notice: Subject to any disclaimer, the term of this patent is extended or adjusted under 35 U.S.C. 154(b) by 734 days.

(21) Appl. No.: 10/699,795

(22) Filed: Nov. 4, 2003

(65) Prior Publication Data
US 2004/0141057 A1    Jul. 22, 2004

(30) Foreign Application Priority Data
Nov. 5, 2002    (IT)    .................... T02002A0950

(51) Int. Cl.
*H04N 7/18*    (2006.01)
*H04N 9/47*    (2006.01)
*H04N 3/14*    (2006.01)
*H04N 5/335*    (2006.01)

(52) U.S. Cl. .................... 348/294; 348/148

(58) Field of Classification Search .......... 348/294, 348/302, 308, 148, 149; 382/104; 250/208.1
See application file for complete search history.

(56) References Cited

U.S. PATENT DOCUMENTS

| | | | | |
|---|---|---|---|---|
| 5,266,828 A | * | 11/1993 | Nakamura et al. | 257/432 |
| 5,313,072 A | * | 5/1994 | Vachss | 250/573 |
| 5,661,303 A | | 8/1997 | Teder | |
| 5,923,027 A | * | 7/1999 | Stam et al. | 250/208.1 |
| 6,130,421 A | * | 10/2000 | Bechtel et al. | 250/208.1 |
| 6,281,806 B1 | * | 8/2001 | Smith et al. | 340/901 |
| 6,396,397 B1 | | 5/2002 | Bos et al. | |
| 6,587,573 B1 | * | 7/2003 | Stam et al. | 382/104 |
| 6,611,610 B1 | * | 8/2003 | Stam et al. | 382/104 |
| 2002/0039065 A1 | * | 4/2002 | Hsiang | 340/435 |
| 2004/0057117 A1 | * | 3/2004 | Hodge et al. | 359/614 |

FOREIGN PATENT DOCUMENTS

| | | |
|---|---|---|
| DE | 42 00 057 A1 | 7/1993 |
| DE | 197 04 818 A1 | 8/1997 |
| DE | 197 55 008 A1 | 7/1999 |
| GB | 2311602 A * | 10/1997 |
| WO | WO 00/53466 | 9/2000 |

* cited by examiner

*Primary Examiner*—Justin P Misleh
(74) *Attorney, Agent, or Firm*—Sughrue Mion, PLLC

(57) ABSTRACT

The invention describes a system with a multifunctional integrated visual sensor using a CMOS or CCD technology matrix having a sensitive area divided into sub-areas dedicated to a series of specific functions.

22 Claims, 14 Drawing Sheets

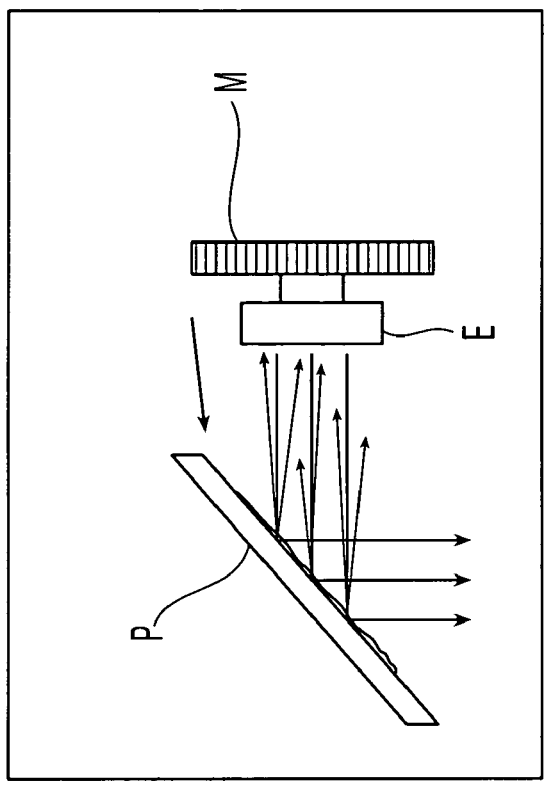
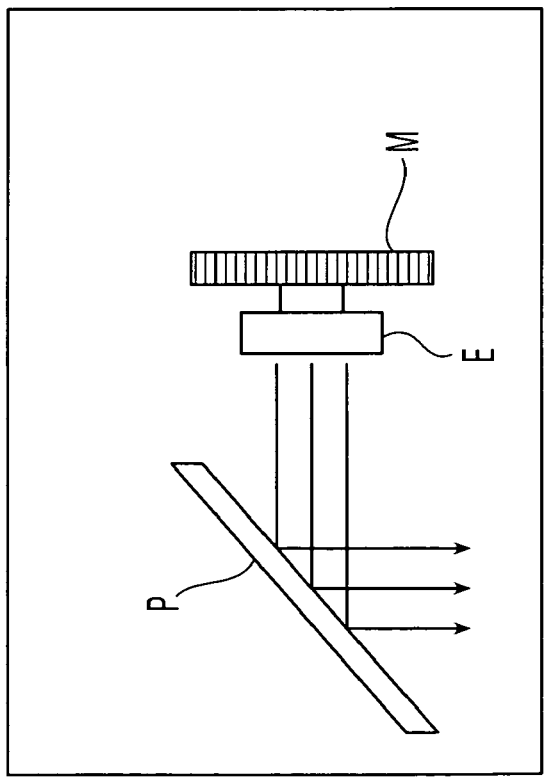
Fig. 3
Fig. 2

MULTIFUNCTIONAL INTEGRATED VISUAL SYSTEM WITH CMOS OR CCD TECHNOLOGY MATRIX

BACKGROUND OF THE INVENTION

The present invention relates to a visual system, in particular for use on motor cars, for detecting environmental parameters, such as a misting of the motor vehicle windscreen, or the presence of rain drops on the windscreen, or low lighting conditions when going through a tunnel, under a bridge or due to dusk, or the presence of mist and fog, or the meeting with another vehicle, said system to be used also for monitoring the scene before the vehicle ("front monitoring"), in order to detect for instance the presence of a bend with such a time anticipation to cause the movement of the adaptive headlight before the bend begins, or to signal a side movement of the vehicle towards lane-marking lines ("lane warning").

SUMMARY OF THE INVENTION

The aim of the present invention is to carry out a relatively simple and reliable system that can efficiently perform all or part of the aforesaid functions. A further aim is to overcome current systems for motor vehicles providing for package integration of different sensors.

In the light of achieving said aim, the object of the invention is a multifunctional visual system comprising a CMOS (or CCD) technology visual matrix having a sensitive area divided into sub-areas each designed for one or more functions in the monitoring of the scene or in the detection of environmental parameters. The division into sub-areas takes place through integration of several optical "imaging" systems and other optical systems.

The invention aims in particular at integrating into a motor vehicle a visual system of the type referred to above, using a monochromatic, linear or logarithmic VGA CMOS matrix, to be placed for instance close to the inner rear-view mirror of the motor vehicle, so as to perform several functions among: rain detection, misting detection, fog detection, dusk detection, detection of driving in a tunnel, detection of meeting with another vehicle, front monitoring.

The detection of some environmental parameters, such as fog and rain, can be carried out both with an active technique, i.e. with an emitter, as shall be disclosed in further detail in the following, and with a passive technique, i.e. without emitter.

In first simpler embodiment of the visual system with CMOS matrix according to the invention, said matrix has its sensitive area divided into specific sub-areas designed for front monitoring, for passive fog detection, for dusk detection, for detection of driving in a tunnel and for active fog detection, respectively.

In a second more complex embodiment, the sensitive area of the matrix also includes a specific sub-area for rain and misting detection.

In a still more complex third solution, the sensitive area of the matrix also comprises another specific sub-area for detecting the meeting with another vehicle.

Still according to a preferred feature of the invention, the system is equipped with a sub-area dedicated to an active rain detection by means of an emitter. Preferably, said area dedicated to rain function is also dedicated to windscreen misting function, always by means of an emitter.

Still according to a further preferred feature, dusk function is performed by a specific sub-area of the CMOS matrix. Tunnel function is performed by using part of the area dedicated to front monitoring function. Fog function is performed both through a dedicated sub-area with an active technique (i.e. via an emitter, for instance a LED or laser diode) and with a passive technique in another sub-area, the latter being included in the one dedicated to front monitoring.

Vehicle meeting function is performed by using two dedicated sub-areas, each having its own system of lenses and filters, or a sub-area dedicated to front monitoring, by means of optical filters laid with a discretization degree at pixel level.

Still according to the invention, it is also provided that the sensor has a protection window made of glass or transparent plastic material, which also acts as support for optical fibers and, if necessary, a prism; these optical components are fitted into holes made into said window, whose function shall become apparent in the following.

Still according to a further feature of the invention, it is provided for an optical insulation system between the area dedicated to front monitoring and those dedicated to rain, misting, fog and dusk functions, based on a partial covering of the surface of the matrix protection window, on the side towards the matrix, with a layer made of absorbing or reflecting material, for instance through serigraphy on thermal evaporation.

Still according to a further feature of the invention, it is provided for an optical insulation system of the area dedicated to rain function from the influence of the objective for front monitoring function, which insulation is based on a partial covering of some faces of the prism with a layer made of absorbing or reflecting material, for instance through serigraphy or thermal evaporation.

As far as the sub-area dedicated to rain function is concerned, the sensor is associated in series with a prism provided with optical insulation, an optical band-pass filter, an objective oriented perpendicularly to vehicle windscreen.

As far as windscreen misting function is concerned, which is designed to enable the automatic start of demisting means the vehicle is equipped with, the corresponding sub-area is associated in series with a prism provided with optical insulation, a filter and an objective oriented perpendicularly to vehicle windscreen.

For dusk function it is provided for an optical fiber made of plastic or glass for collecting light, oriented perpendicularly to vehicle windscreen or with a deviation of some degrees from this position.

For tunnel function it is provided for an objective, oriented towards the front scene, with a focal length suitable for front monitoring function.

For fog function based on an active technique it is provided for a "ball" or "grin" lens, or also no lens at all, together with an optical fiber, if necessary with another "grin" or micro-optical lens, or also with no lens at all, together with a high-pass/interferential filter, with a collection lens whose optical axis is orthogonal to vehicle windscreen or front scene. For fog function based on passive technique it is provided for an objective oriented towards the scene before the vehicle, with a focal length suitable for front monitoring function.

For vehicle meeting function it is provided for an optical filter (high-pass filter >500 nm or low-pass filter <500 nm) together with an objective for each of the two sub-areas.

For front monitoring function it is provided for an objective with suitable focal length, whose optical axis is inclined of some degrees with respect to the horizontal plane, oriented in motion direction and at a given distance from matrix center.

Obviously, output signals from matrix visual system are directed towards an electronic system acquiring images concerning the various sub-areas (through "windowing" in the case of CMOS cameras) and then processing them.

BRIEF DESCRIPTION OF THE DRAWINGS

Further characteristics and advantages of the invention shall be evident from the following description referring to the accompanying drawings, provided as a mere non-limiting example, in which:

FIGS. 2, 3 are schematic views showing the operating principles of the sensor detecting windscreen misting.

DETAILED DESCRIPTION OF THE INVENTION

Figure 1:
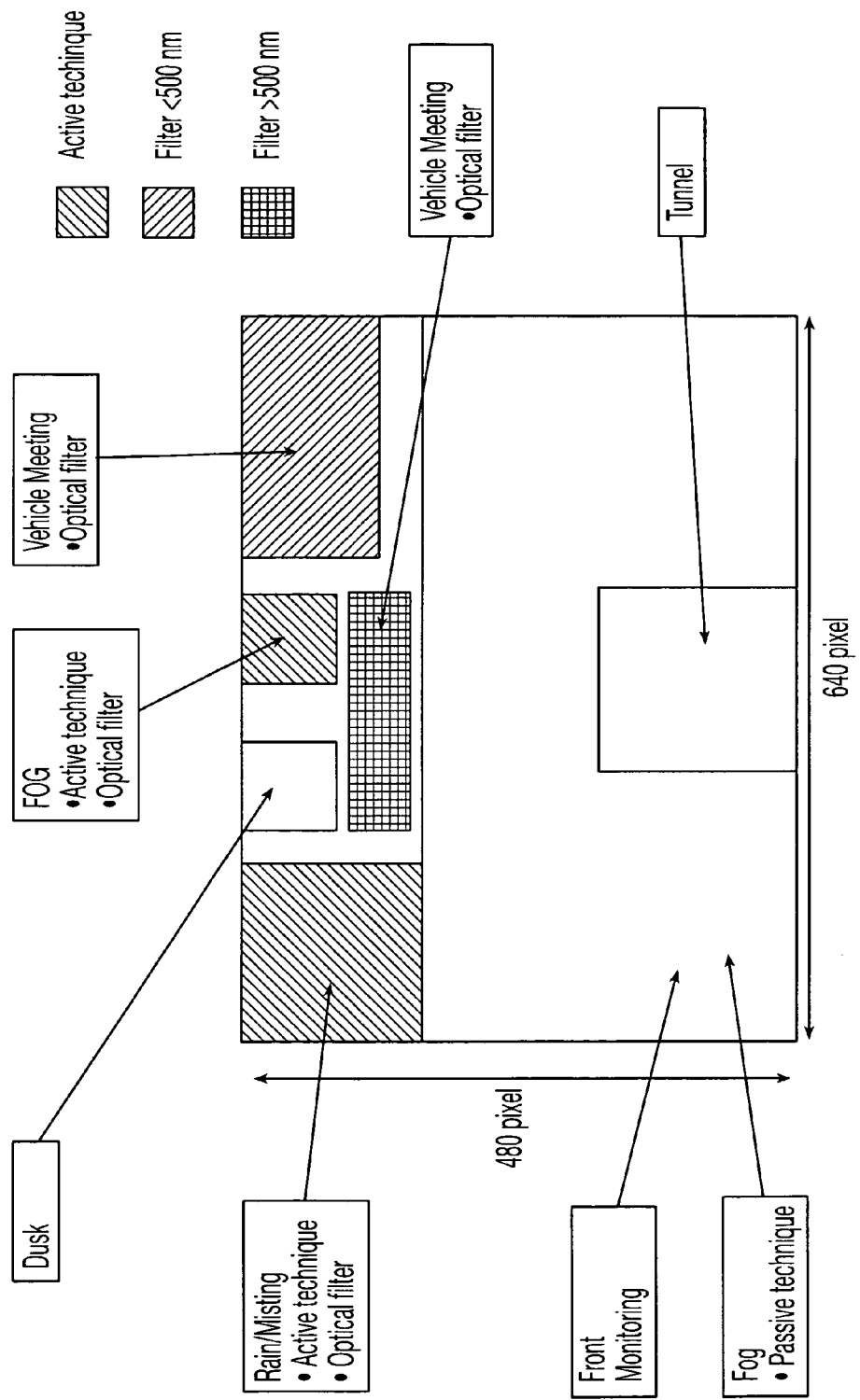
FIG. 1 is a schematic view of a first embodiment of the matrix sensor according to the invention implementing all functions discussed above.

FIG. 1 of the accompanying drawings shows a preferred embodiment concerning the division of the sensitive area of the CMOS matrix of the sensor according to the invention into sub-areas dedicated to one or more functions. This embodiment takes into consideration all functions mentioned above: front monitoring, vehicle meeting, rain, misting, fog (active and passive mode), dusk, tunnel.

FIG. 1 shows the sensitive area of a VGA matrix with a hint to the functions performed by each sub-area and their features.

The distribution of the various sub-areas takes into consideration some basic criteria:

1. The inclination of the matrix when mounted onto the inner rear-view mirror of the motor vehicle depends on the direction of the optical axis for performing scene front monitoring function;

2. For each function the size of the areas is function of the fields of view and of the required resolution;

3. The positions of the areas depend on the direction of the optical axis of each function and on the need for separation areas in which pixels are not used;

4. A single area can be dedicated to more functions; or a portion of the area dedicated to one function can also be dedicated to another function.

Possible measuring techniques to be used for developing the functions referred to in FIG. 1 will now be described—

Windscreen Misting

Passive system: on windscreen outer surface lies a reference image, for instance a grid, which is focused onto the CMOS matrix. The sharpness level of the image depends on the misting degree of windscreen inner surface. The critical points of this technique are the following: the sensitivity to misting levels that cannot be seen by human eyes; the dependence of the signal on environmental lighting.

Active system:—as shown in FIGS. 2, 3, an infrared emitter E sends a bundle onto the inner surface of the glass of motor vehicle windscreen P, with an angle of incidence of about 45°. If the surface is misted up, the bundle is partially backscattered by condensate droplets (FIG. 3) and detected by CMOS matrix M. If no misting is present (FIG. 2), the aforesaid phenomenon does not occur. The optical system can shape the bundle sent out by emitter E (typically a LED) so that it is focused onto a convenient windscreen portion.

Rain

The CMOS matrix detects the image of drops lying on windscreen outer surface. A quantitative analysis can be carried out on a single image, for instance by considering the spectrum in space frequency, or by comparing consecutive images with statistical methods. In order to eliminate the dependence on outer lighting conditions, which affect drop contrast, and to light up in a uniform and time-constant way the concerned windscreen area, a LED source in near-infrared radiation and a band-pass filter adjusted on LED wavelength are used.

Dusk/Tunnel

Figure 4:
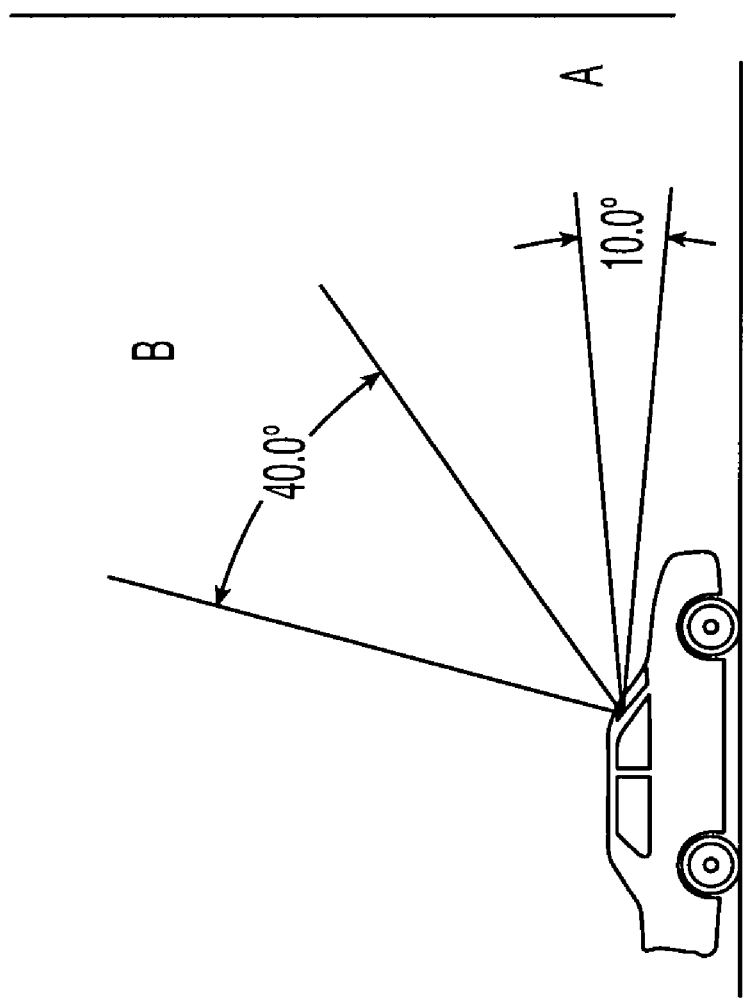
FIG. 4 is a schematic view referring to the configuration of the sensor for dusk/tunnel function.

Two matrix areas are dedicated to lighting measures carried out from two different directions (see FIG. 4):
small solid angle A in driving direction (for instance 10°);
larger solid angle B (for instance 40°) oriented upwards, so as to achieve a measure of average lighting around current vehicle position.

Fog

Passive sensor: passive fog detection is performed by scene image acquisition in the area destined to front monitoring and subsequent analysis of image sharpness. It enables to detect the fog bank in advance with respect to active system, which has a limited range of action.

Figure 5:
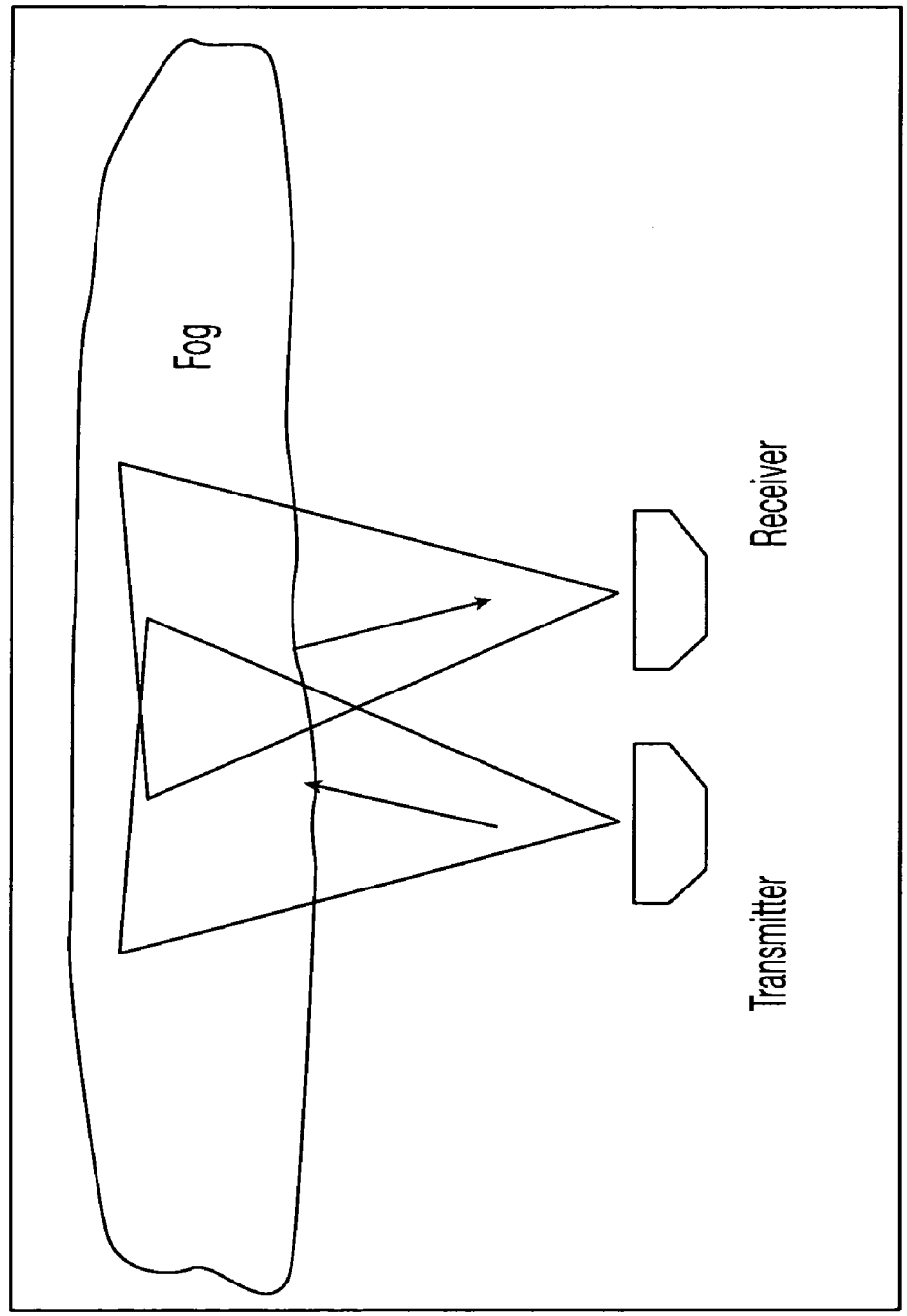
FIG. 5 is a general diagram showing active fog detection.

Active sensor: the visibility sensor comprises a transmitting module (LED or laser diode in infrared radiation) and the receiving module (CMOS camera). The two fields of view partially overlap. In case of fog, the droplet concentration in the overlapping area causes a backscattering of the bundle, which is detected by the sensor (FIG. 5).

Vehicle Meeting

The CMOS camera frames some portions of the road scene before the vehicle. The matrix of FIG. 1 includes two "Vehicle meeting" areas respectively dedicated to the detection of the headlights of vehicles driving in opposite direction and of the rear-lights of vehicles driving in the same direction. For the two areas convenient high-pass and low-pass filters for distinguishing dipped headlights from rear-lights are used. An alternative consists in using the area designed for front monitoring in a color matrix or in a monochromatic matrix by laying at pixel level the necessary optical filters, though only in the matrix area or sub-areas designed for front monitoring.

Scene Front Monitoring

The main portion of the matrix of FIG. 1 is used to frame the road scene before the vehicle and to implement functions such as lane warning, adaptive headlight and vehicle meeting.

Figure 6:
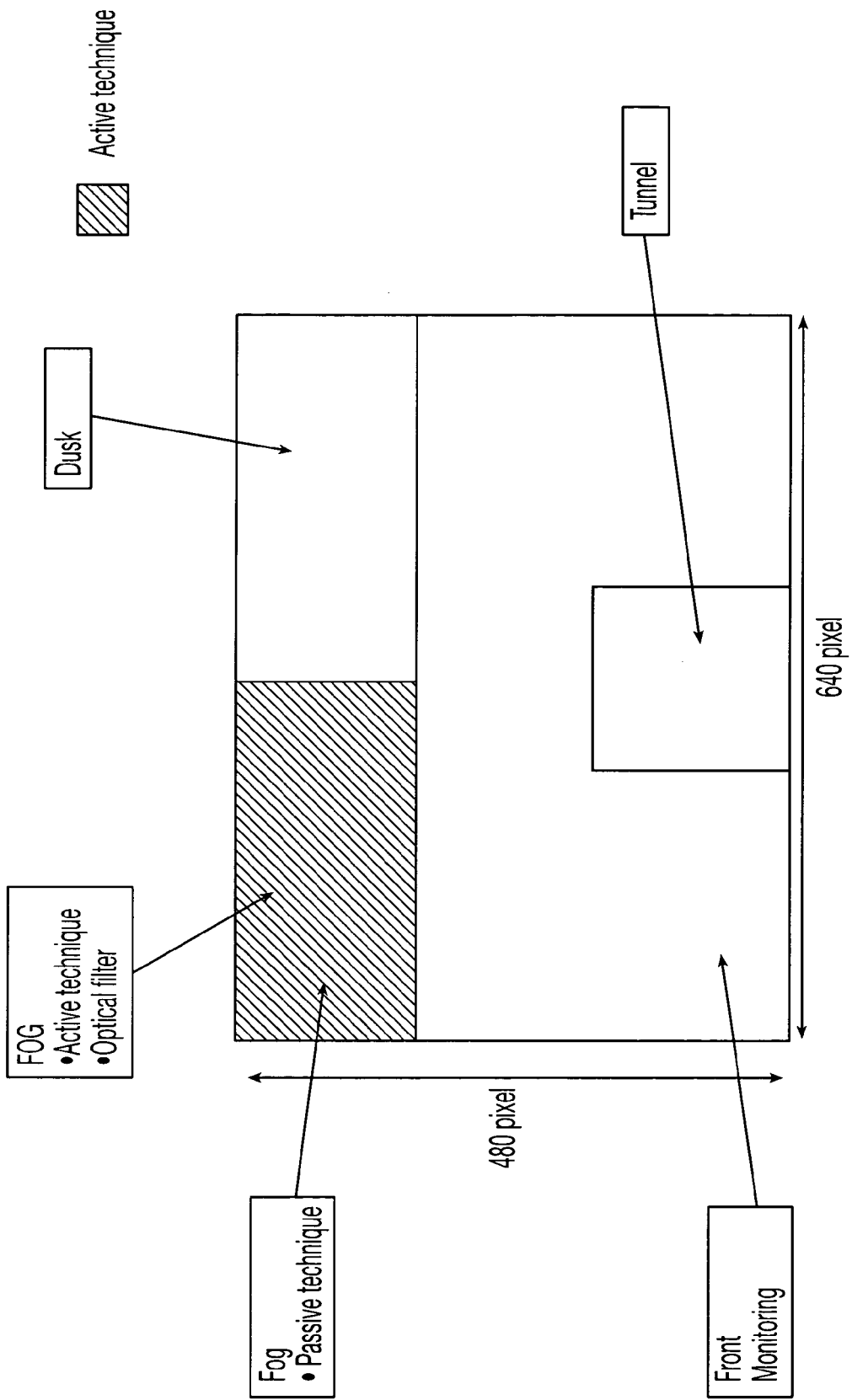
FIGS. 6, 7 show a second and a third embodiment of the system according to the invention, implementing a smaller number of functions.

The embodiment shown in FIG. 6 is a simplified embodiment with respect to the one in FIG. 1, and includes only sub-areas for front monitoring, tunnel, fog (active and passive technique) and dusk functions.

Figure 7:
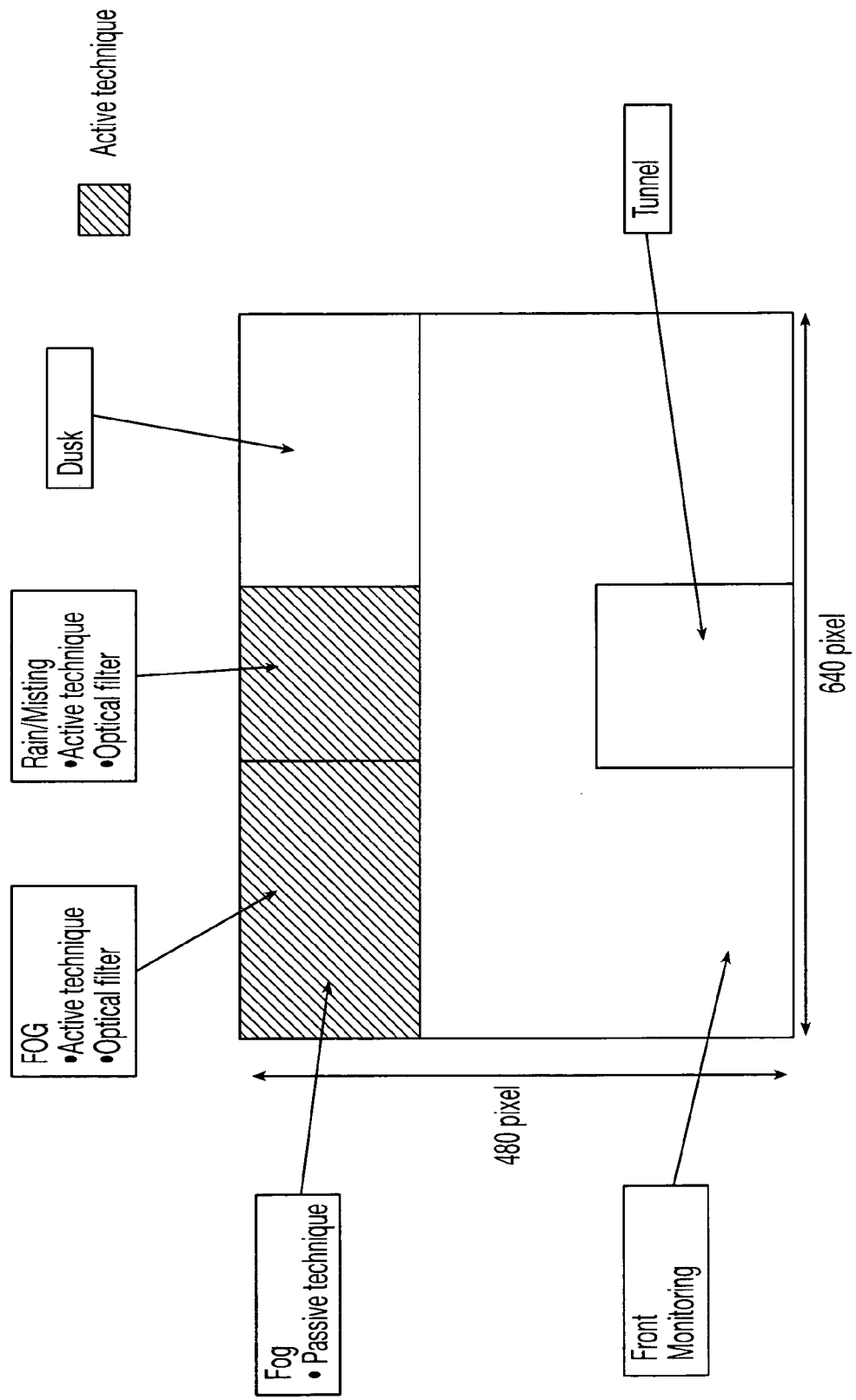

FIG. 7 shows a further embodiment envisaging in addition also rain/misting function.

CMOS Matrix

As far as CMOS visual matrix is concerned, the main requirements it should meet for the multifunctional integration proposed in the previous paragraphs are the following:

VGA format: this format enables a division of the matrix into seven used areas and into separation areas in which pixels are not used;

pixel size: a very small pixel size implies a higher difficulty in carrying out dedicated optical systems for each function/area;

monochromatic or color: the use of a color matrix would avoid the use of optical filters required for "vehicle meeting" function, however to the detriment of space resolution capability;

linear or logarithmic response: some functions are based on the quantitative assessment of a parameter for which it would be better to have a linear response of the sensor and constant integration time; as far as the dynamic range is concerned, however, it is preferable to use a sensor with logarithmic response.

dynamic range: front monitoring functions require that the sensor is able to cover an illumination range above 80 dB since typical scenes can involve situation varying from dusk to direct sun rays;

sensitivity: this is an important parameter for front monitoring functions during night driving with a low illumination level (for instance dusk=1 lux) or for fog function when the backscattering radiation collected is very small (in the range of nW);

spectral response: the sensor should have a good response in the range 800-900 nm (used for active functions—where the windscreen glass of a standard motor vehicle has a transmittance of about 30%); for "dusk" function the sensor should have a response as similar as possible to the one of human eyes (photometric response);

frame rate: frame rate is not a critical parameter unless fast acquisitions by means of windowing are to be made and then digital filtering techniques are then to be implemented (for instance in the case of vehicle meeting function, in which it would be useful to cut the modulated radiation coming from AC-supplied light sources with frequencies of 50-60 Hz).

In a practical example of embodiment of the invention, a logarithmic monochromatic VGA CMOS camera has been used, carried out with CMOS technology 0.35 micron. It integrates the matrix of active pixels, amplification stages, a 10 bit AD converter and the interface for a microprocessor. The photodiode matrix continuously converts radiation into voltage (without charge integration as typical of linear CMOS) and pixels can therefore be read at any moment.

The current generated by the photodiodes has a linear dependence on the intensity of the incident radiation. The supply circuit of the photodiode has a logarithmic feature so that pixel voltage output is proportional to the logarithm of the incident radiation.

Figure 7A:
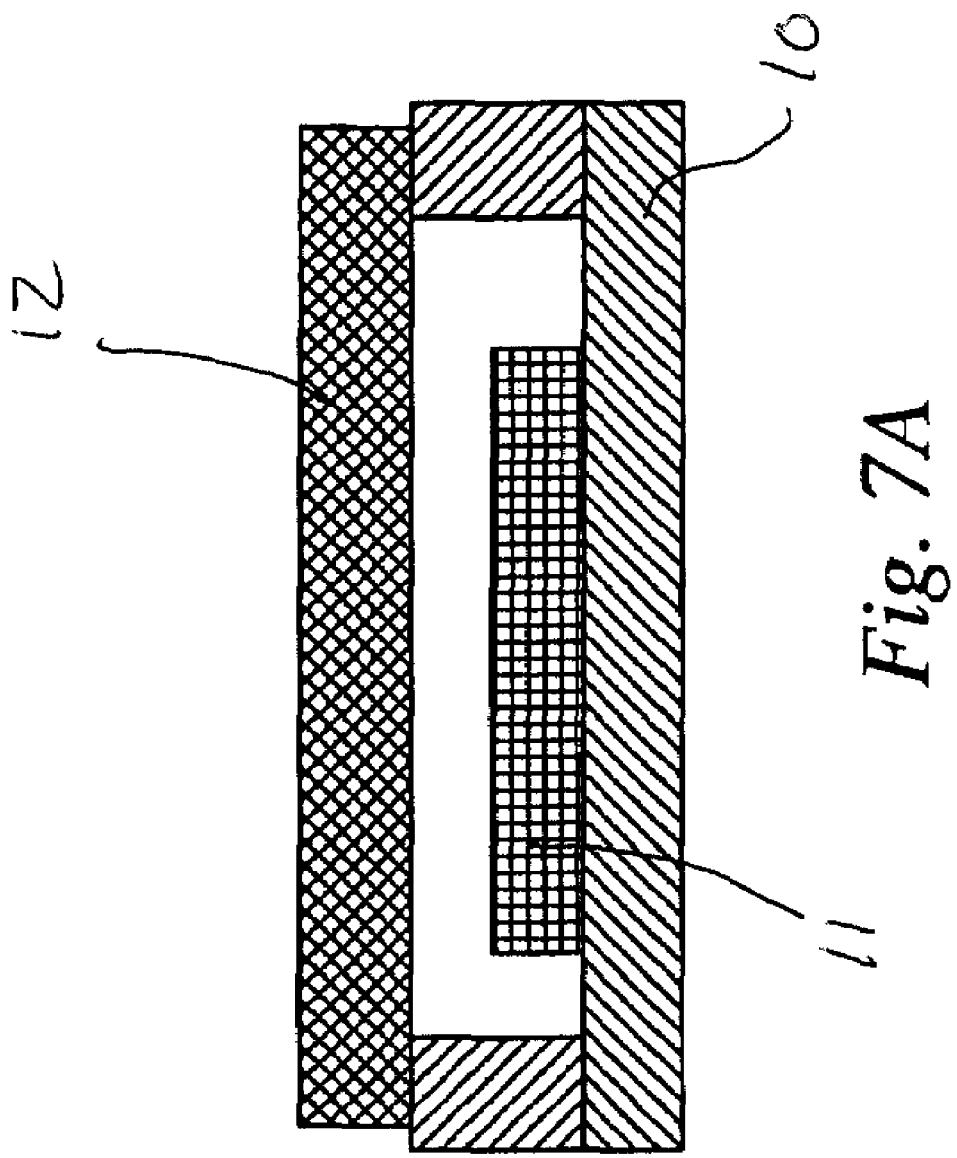
FIGS. 7A, 7B show a schematic sectioned view and a plan view of the sensor belonging to the system according to the invention.
Figure 7B:
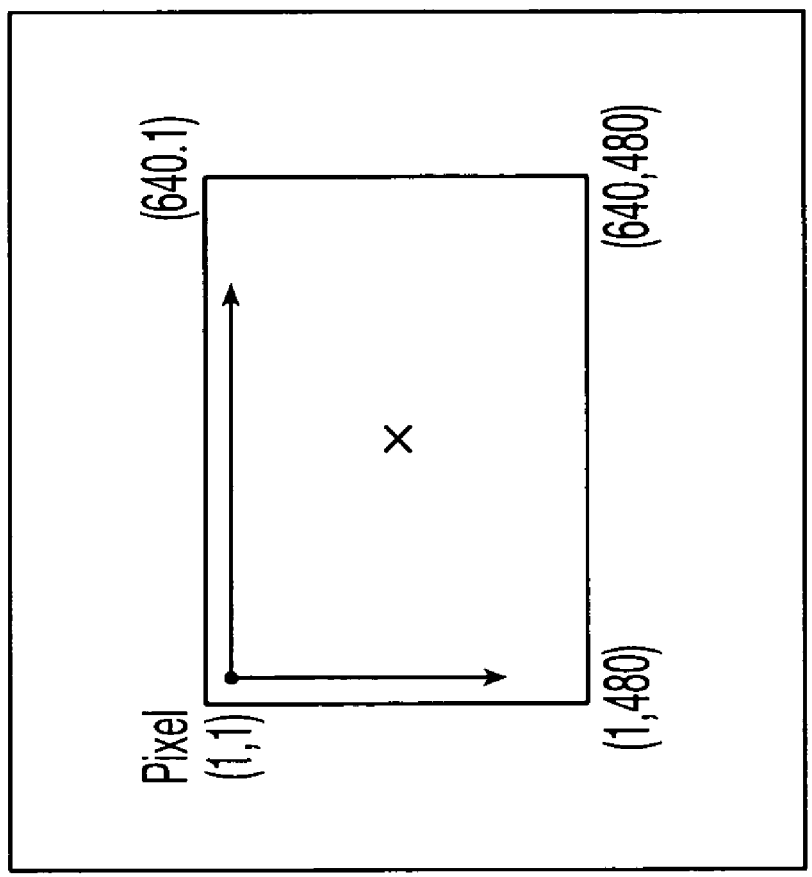

With reference to sensor package, the latter is shown in FIG. 7A (in lateral section) and in FIG. 7B (showing a view from above). Said package comprises a base 10 onto which the sensor chip 11 is mounted, and an optical protection window 12, consisting of a substrate of transparent material, with plane and parallel surfaces. The CMOS matrix is associated to optical components designed to optimize the signal collected by the integrated sensor for each of the environmental monitoring functions; in the case of rain, vehicle meeting and front monitoring functions, the optical components should also carry out a scene imaging. For each function the field of view and the dedicated sensor area determine the focal length of the optical component to interpose. Once the focal length has been set, the requirements concerning the illumination level limit the minimum dimension of the lens. The conditions imposed by system geometry should further be taken into consideration. As a matter of fact, each of the adjacent areas a matrix is divided into is associated to an independent optical system. On a design level this kind of integration implies other two conditions:

the optical systems should be placed one beside the other. This limits the size of single components. In the evaluation of the limits possible mechanical solutions for mounting and packaging operations should also be considered;

the proximity of the areas results in disturbances among the signals of the single functions, due to the partial overlapping of image planes. Concerning this problems, a separation system for the single areas should be designed.

Another feature to be taken into consideration is the orientation of the optical axis for every function. It is evident that to meet all requirements it is necessary to find solutions for changing the direction of the optical axis. To this purpose the invention, as shall be evident in the following, uses prisms and optical fibers.

Since for all functions the distance of the target spot is over 10 times focal length, the distance optical system-sensor (image spot) shall be approximately the same as focal length, which for "rain", "dusk" and "vehicle meeting" (detection of rear-lights) functions is below 5 mm. This distance is a strict requirement, especially if prisms are to be placed between the objective and the sensor.

Figure 8:
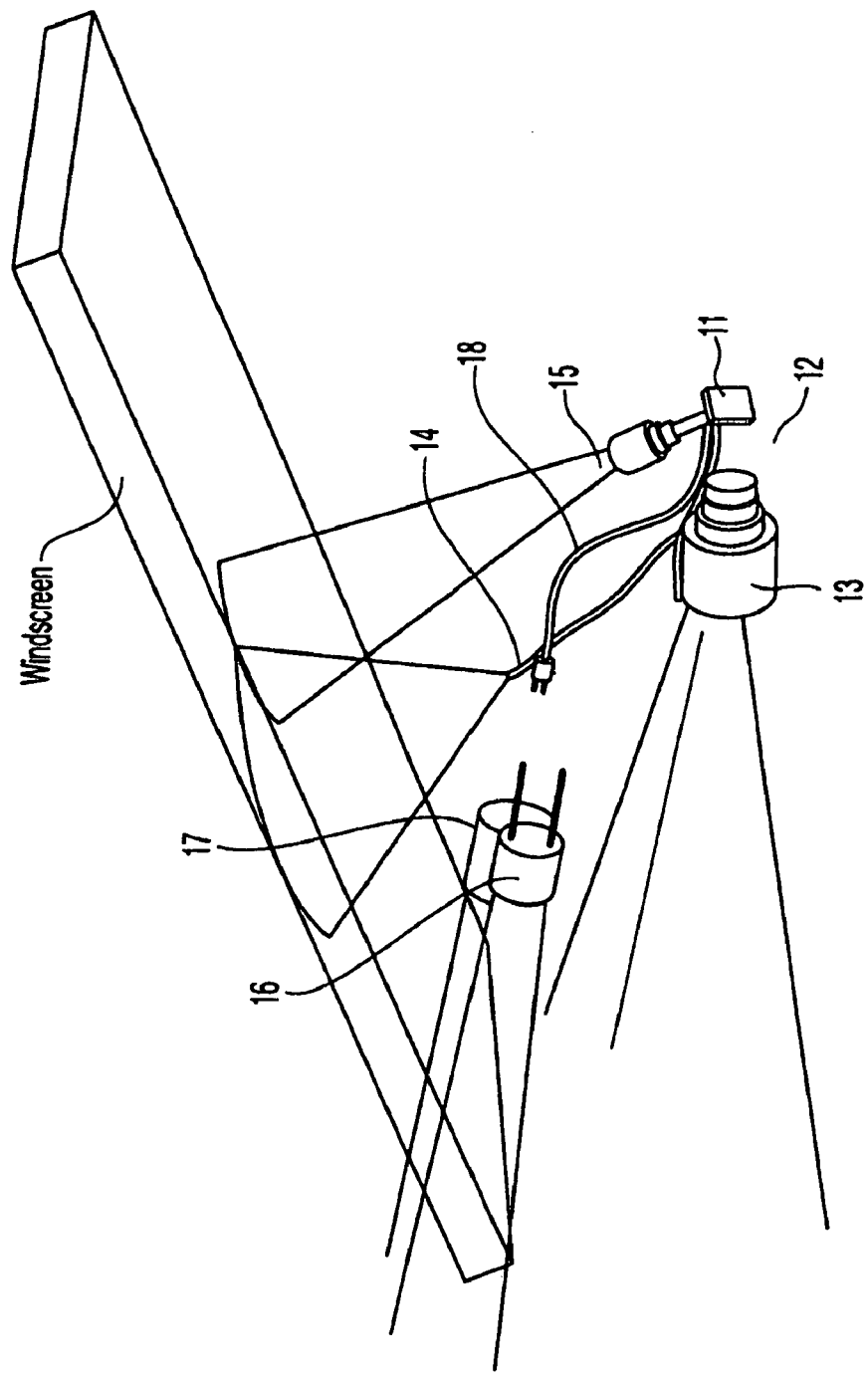
FIG. 8 shows a perspective view of an example of embodiment of the system according to the invention.

FIG. 8 shows a perspective view of an embodiment of the system according to the invention. The CMOS matrix 11 equipped with protection window 12 is associated to an objective 13 for front monitoring. As was already referred to, the objective 13, together with the sensor 11, is mounted in the front portion (i.e. in driving direction) of the inner rear-view mirror of the motor vehicle (not shown for reasons of clarity). In an example of embodiment, the objective 13 has a negative lens as first element, so as to cover quite a wide field of view (35°-45°).

Then there is the problem concerning the insulation of front monitoring function. A possible solution involves the use of a separation wall with rectangular opening. The opening has the same shape and size as the front monitoring areas.

Considering now "dusk" and "fog" functions, there is the problem concerning the fact that the optical axis should be inclined upwards for instance of an angle of 60° with respect to motion directions. Detection is of non-imaging type.

For these two functions the invention solves the problem concerning the inclination of the optical axis by using conventional optical fibers, such as the optical fiber 14 in FIG. 8. Such an optical fiber enables to transmit the signal along a path that can also be curved. Said component is further quite cheap. The optical fiber is preferably associated to a lens, for instance a ball lens or a grin lens (gradient of index).

FIG. 8 also shows an objective 15 for rain detection, and an emitter 16 to which a collection lens 17 and an optical fiber 18 for fog detection are associated.

Figure 9:
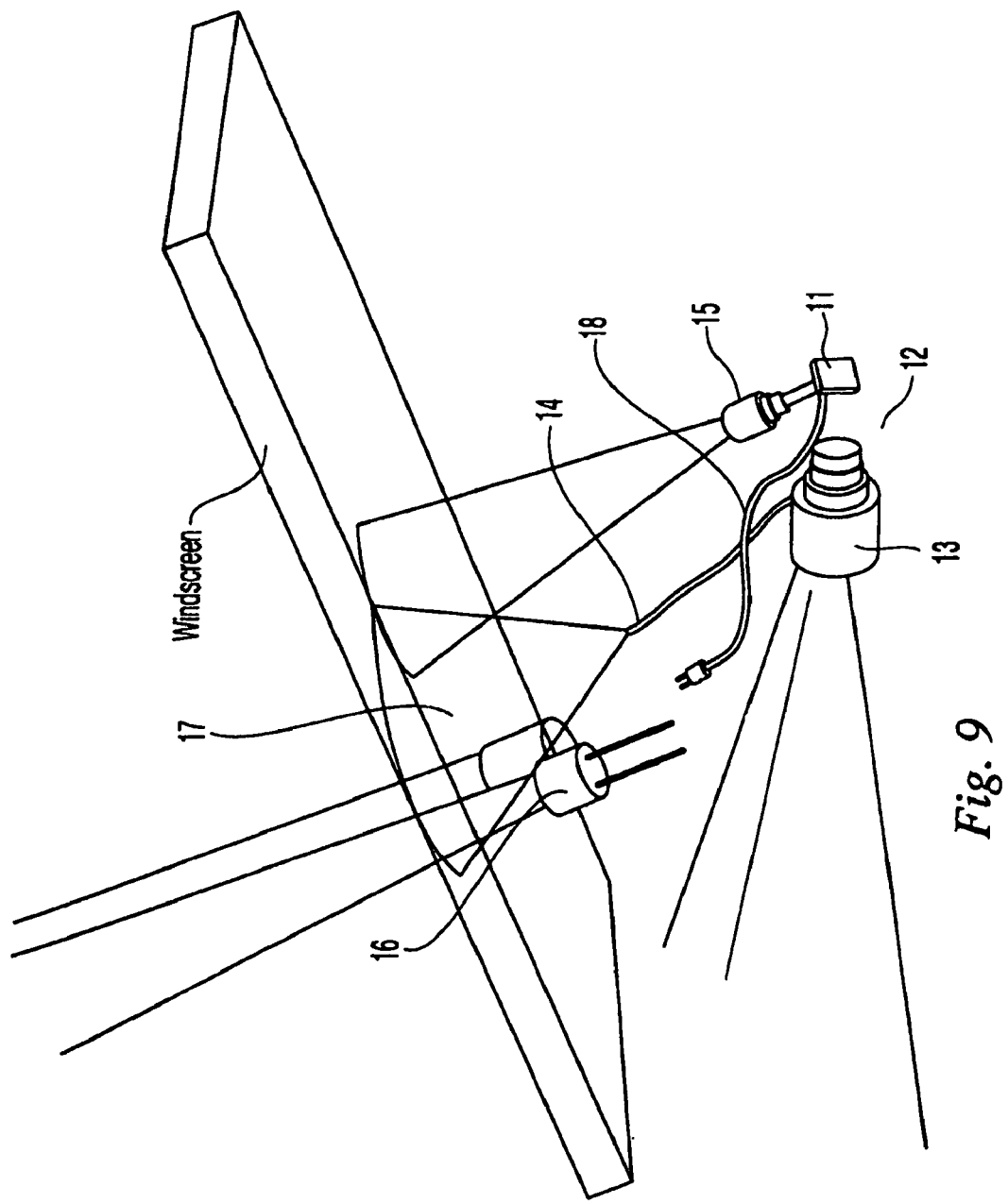
FIG. 9 shows a variant of FIG. 8.

FIG. 9 shows a variant of FIG. 8, in which corresponding elements have the same reference number.

Figure 10:
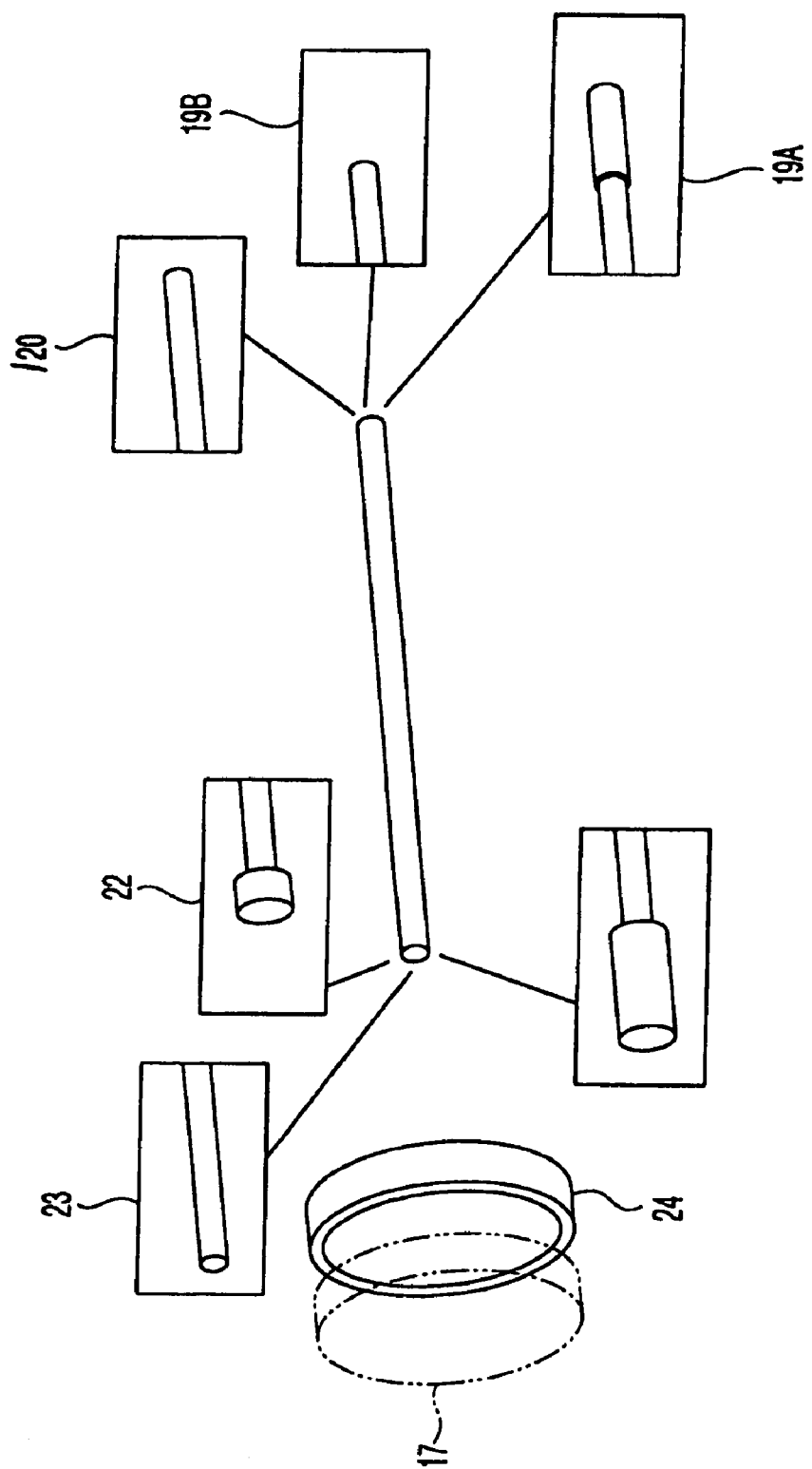
FIG. 10 shows the possible execution variants of the optical system for fog detection.

FIG. 10 shows the various possibility of association to an optical fiber 18 of a GRIN 19A lens or a ball lens 19B, or of leaving the fiber end without lens 120. The opposite end of the fiber 18 can be provided with a GRIN lens, or a micro-optical system 22, being it further possible to leave the end without lens as shown in 23. The collection lens 17 is associated to a band-pass optical filter 24.

Figure 11:
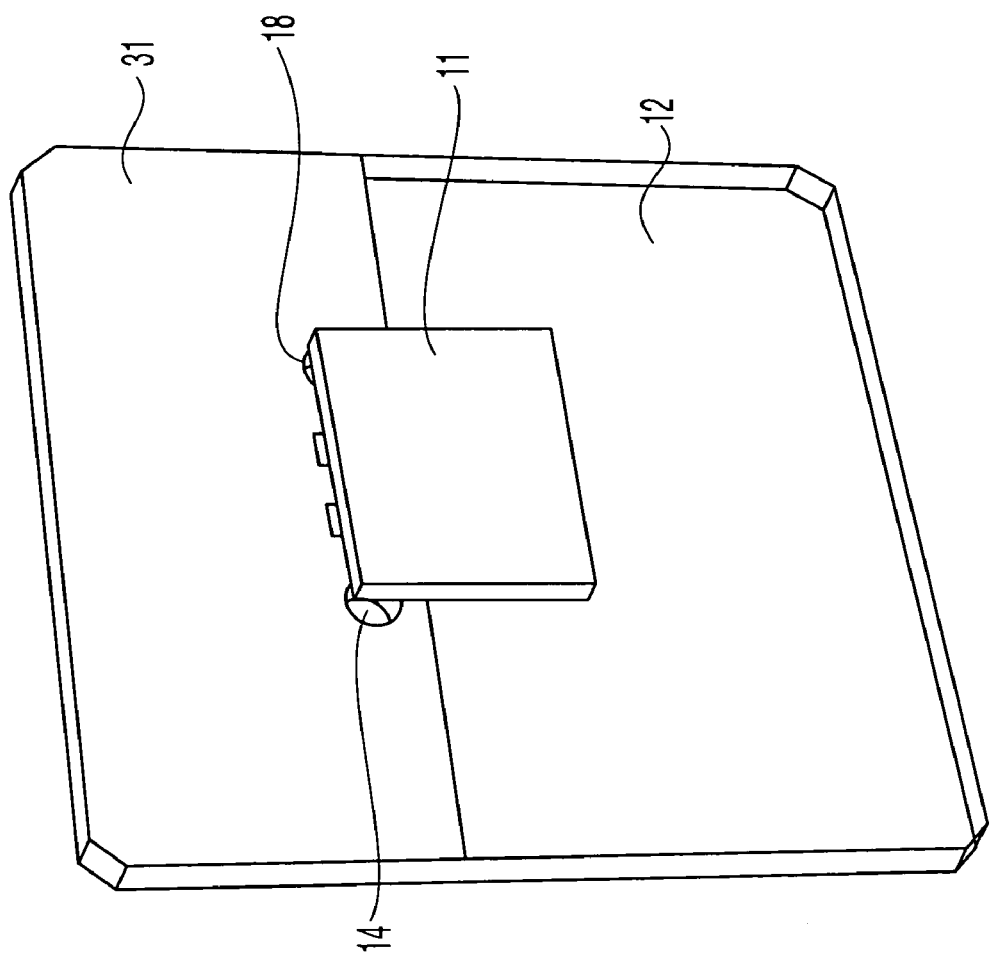
FIGS. 11, 12A, 12B show three different perspective views of the assembly including the sensor matrix according to the invention with the protection window associated thereto.
Figure 12B:
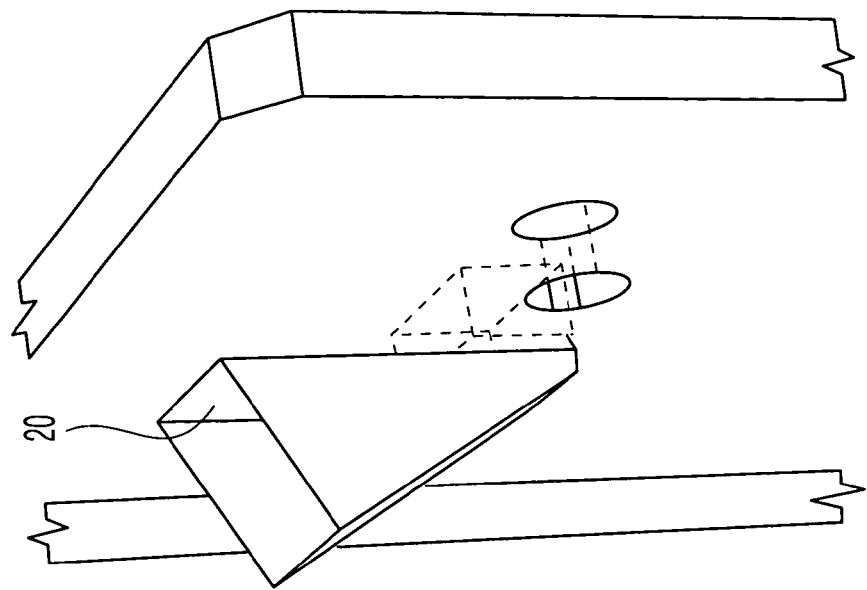
Figure 12A:
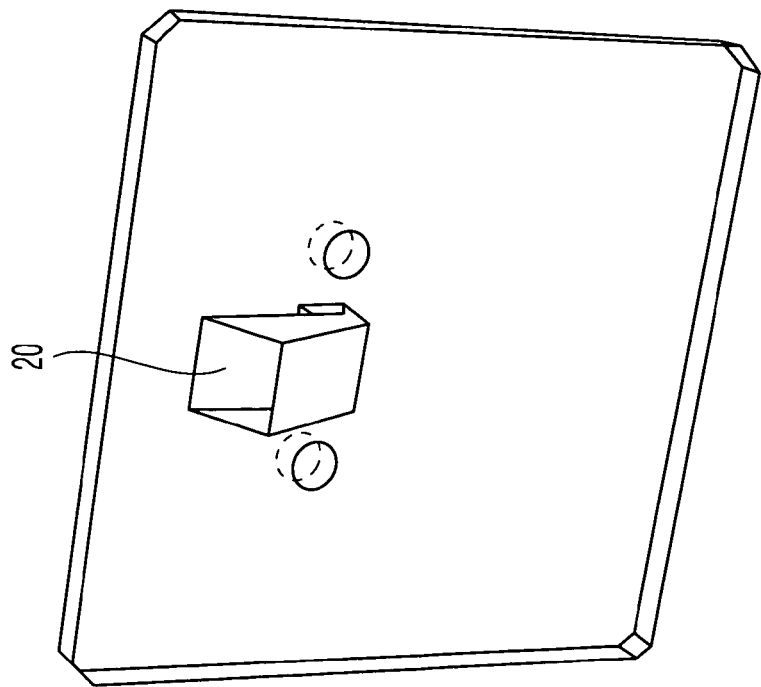

A step following the integration of front monitoring, "fog" and "dusk" functions through objective and optical fibers, consists in the additional integration of "rain" function. For the latter function imaging optical components are necessary, i.e. lenses and prisms. The field of view of front monitoring function has an optical axis inclined of some degrees downwards. For "dusk", "rain" and "fog" functions the inclination is of 60 degrees upwards. Actually, for the latter three functions there is a broad tolerance. A variation of 5-6 degrees does not involve any substantial change as far as functionality is concerned. A possible optical solution is to keep matrix plane orthogonal to the optical axis of front monitoring function and, by means of prisms, to change the direction of the optical axis for the other three functions. The tolerance range for orientation enables to select a prism deviating the optical axis of 60° with respect to the perpendicular to image plane (matrix plane). The prism taken into consideration (Littrow prism) is referred to with 20 in FIGS. 12A and 12B. FIG. 11 shows the shaded area 31 and the end portions of optical fibers 14 and 18 fitted into holes made into the optical window 12.

Figure 13:
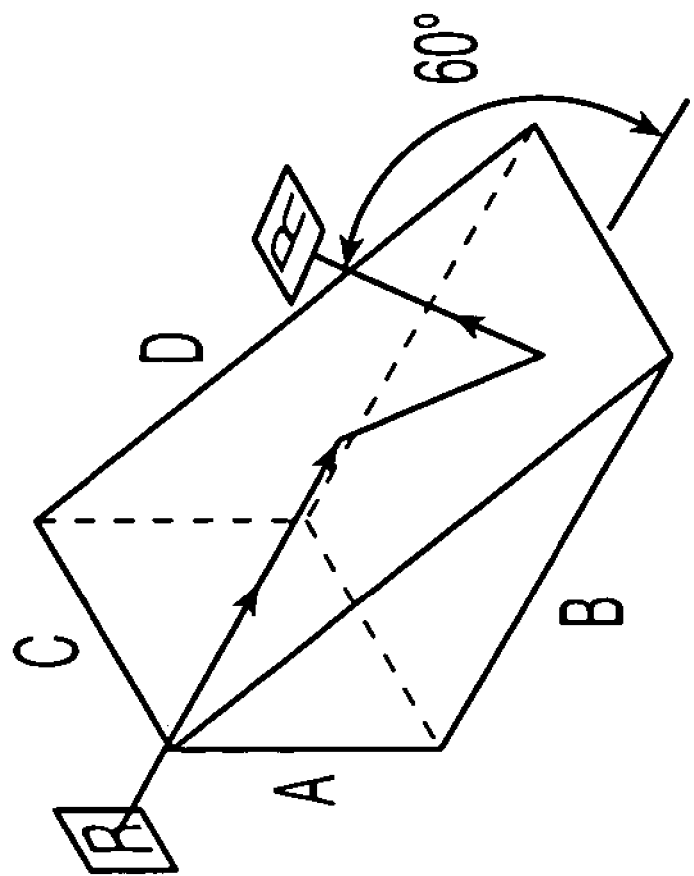
FIG. 13 is a perspective view of a prism used in the system for rain detection according to the invention.

FIG. 13 shows a perspective view of the prism 20. Said prism 20 is made of glass or transparent plastic, with its face BC covered by a one- or multi-layer coating, so as to obtain a surface reflecting towards the inside of the prism and absorbing or reflecting to-wards the outside. The triangular faces ABD of the prism 20 should be covered with a one- or multi-layer coating, so as to obtain a surface absorbing towards the inside of the prism and absorbing or reflecting to-wards the outside.

The prism 20 should be oriented as in FIG. 12, with its face AD parallel to sensor plane; the face CD should further not rest on any optical element, for reasons that shall be evident in the following. Before the face AC of the prism 20 the imaging objective 15 should be placed, which should have such a rear focal length to be able to focus beyond the prism. The light getting out of the objective strikes the face AC and gets into the prism 20; if the angle of incidence onto AC is smaller than a limit angle (which for prism-air passage is of 27.9° with a refractive index of the prism of 1.5), light is reflected wholly onto the face CD; this results in the need for air as optical medium outside the face CD. Eventually, the bundle gets out of the prism 30 through CD towards the sensor.

For the optical insulation of the bundle getting out of the prism 20, a rectangular opening having the same surface as the section of the radiation bundle getting out of the prism 20 or a larger surface, should be made into the optical protection window 12. The inner wall of the opening should be covered with an absorbing coating, so as to avoid disturbances with the signal of front monitoring function. If necessary, all inner walls can be covered with said coating in case of disturbances with the signals from the optical fibers.

This kind of optical system (objective plus prism) can also be used together with the objective for front monitoring function. The fact that the two optical systems do not have the same axis is advantageous as far as size is concerned.

Obviously, though the basic idea of the invention remains the same, construction details and embodiments can widely vary with respect to what has been described and shown by mere way of example, however without leaving the framework of the present invention.

What is claimed is:

1. A visual system, comprising:
a CCD or CMOS matrix having a sensitive area, and
a plurality of optical devices with different directions, fields of view or modes of optical separation,
wherein said sensitive area of the matrix is divided into a plurality of separated sub-areas designed for different specific functions, a first part of said plurality of separated sub-areas being dedicated to scene monitoring and a second part part of said plurality of separated sub-areas being dedicated to detection of environmental parameters, said division being achieved by said plurality of optical devices,
wherein a fog function is performed in one of the dedicated sub-areas in the second part with an active technique for local fog detection, and in one of the dedicated sub-areas in the first part with passive technique for fog bank detection.

2. The visual system according to claim 1, wherein the system is installed in a motor vehicle on a front portion of an inner rear-view mirror of the motor vehicle, and wherein additional sub-areas in the second part perform rain detection, windscreen misting detection, and dusk detection, respectively.

3. The visual system according to claim 1, wherein the matrix is a linear or logarithmic, monochromatic or color VGA CMOS matrix.

4. The visual system according to claim 1, wherein at least one of the sub-areas in the first part is designed for front monitoring.

5. The visual system according to claim 1, wherein one of the sub-areas in the second part is for rain and misting detection.

6. The visual system according to claim 1, wherein one of the sub-areas in the first part is for meeting detection.

7. The visual system according to claim 5, wherein the sub-area dedicated to rain and misting detection includes an emitter.

8. The visual system according to claim 1, wherein one of the sub-areas in the second part is for a dusk function.

9. The visual system according to claim 4, wherein the at least one sub-area dedicated to front monitoring also performs a tunnel function.

10. The visual system according to claim 1, wherein the sub-area dedicated to the fog function, based on the active technique, receives an optical signal through an optical system comprising one of a ball and grin lens, an optical fiber, a high-pass or interferential filter, and a collection lens.

11. The visual system according to claim 10, wherein the sub-area dedicated to the fog function, based on the passive technique, receives the optical signal through an objective dedicated also to a front monitoring function.

12. The visual system according to claim 1, wherein some sub-areas are reserved for unused pixels to provide separation between used sub-areas.

13. A visual system, comprising:
a CCD or CMOS color or monochromatic matrix having a sensitive area, and
a plurality of optical devices with different directions, fields of view or modes of optical separation, wherein said sensitive area of the matrix is divided into a plurality of separated sub-areas designed for different specific functions, a first part of said plurality of separated sub-areas being dedicated to scene monitoring and a second part of said plurality of separated sub-areas being dedicated to detection of environmental parameters, said division being achieved by said plurality of optical devices, wherein a vehicle meeting function is performed by one of the sub-areas in the first part by using an optical filter laid with a discretization degree at a pixel level.

14. A visual system, comprising:

a CCD or CMOS matrix having a sensitive area, and a plurality of optical devices with different directions, fields of view or modes of optical separation, wherein said sensitive area of the matrix is divided into a plurality of separated sub-areas designed for different specific functions, a first part of said plurality of separated sub-areas being dedicated to scene monitoring and a second part of said plurality of separated sub-areas being dedicated to detection of environmental parameters, said division being achieved by said plurality of optical devices, wherein the matrix has a protection window made of one of glass and transparent plastic, the protection window acting as support for one or more optical fibers and a prism, the one or more optical fibers carrying to selected sub-areas of the matrix an optical signal.

15. The visual system according to claim 14, wherein said optical fibers have proximal ends fitted into holes made into said protection window.

16. The visual system according to claim 14, wherein a sub-area dedicated to a rain function receives the optical signal from an optical system comprising, in series, the prism with an optical insulation, a filter and an objective with an optical axis orthogonal to a windscreen.

17. The visual system according to claim 14, wherein a sub-area dedicated to a windscreen misting function receives the optical signal from an optical system comprising, in series, the prism with an optical insulation, a filter and an objective with an optical axis orthogonal to a windscreen.

18. The visual system according to claim 14, wherein two sub-areas dedicated to a vehicle meeting function receive the optical signal through filters together with an objective.

19. The visual system according to claim 14, wherein a sub-area dedicated to a front monitoring function receives the optical signal through an objective with an optical axis shifted with respect to the center of the matrix.

20. A visual system, comprising:

a CCD or CMOS matrix having a sensitive area, a plurality of optical devices with different directions, fields of view or modes of optical separation, wherein said sensitive area of the matrix is divided into a plurality of separated sub-areas designed for different specific functions, a first part of said plurality of separated sub-areas being dedicated to scene monitoring and a second part of said plurality of separated sub-areas being dedicated to detection of environmental parameters, said division being achieved by said plurality of optical devices, one of said sub-areas in the first part being dedicated to front monitoring and others of said sub-areas in the second part being dedicated to rain, misting, fog and dusk functions, and an optical insulation between the first and second parts, the optical insulation partially covering a surface of a matrix protection window, on a side towards the matrix, with a layer of absorbing or reflecting material.

21. A visual system, comprising:

a CCD or CMOS matrix having a sensitive area, and a plurality of optical devices with different directions, fields of view or modes of optical separation, wherein said sensitive area of the matrix is divided into a plurality of separated sub-areas designed for different specific functions, a first part of said plurality of separated sub-areas being dedicated to scene monitoring and a second part of said plurality of separated sub-areas being dedicated to detection of environmental parameters, said division being achieved by said plurality of optical devices, wherein one of the sub-areas in the second part is dedicated to a dusk function and receives an optical signal through an optical fiber.

22. A visual system, comprising:

a CCD or CMOS matrix having a sensitive area, and a plurality of optical devices with different directions, fields of view or modes of optical separation, wherein said sensitive area of the matrix is divided into a plurality of separated sub-areas designed for different specific functions, a first part of said plurality of separated sub-areas being dedicated to scene monitoring and a second part of said plurality of separated sub-areas being dedicated to detection of environmental parameters, said division being achieved by said plurality of optical devices, wherein one of the sub-areas in the first part is dedicated to tunnel function and receives an optical signal through an objective dedicated also to a front monitoring function.

* * * * *